(12) United States Patent
Pedain et al.

(10) Patent No.: US 7,734,326 B2
(45) Date of Patent: Jun. 8, 2010

(54) METHOD AND DEVICE FOR PREPARING A DRAINAGE

(75) Inventors: Christoph Pedain, München (DE); Andreas Hartlep, München (DE)

(73) Assignee: BrainLAB AG, Feldkirchen (DE)

( * ) Notice: Subject to any disclaimer, the term of this patent is extended or adjusted under 35 U.S.C. 154(b) by 900 days.

(21) Appl. No.: 10/464,057

(22) Filed: Jun. 18, 2003

(65) Prior Publication Data
US 2004/0010221 A1 Jan. 15, 2004

Related U.S. Application Data

(60) Provisional application No. 60/437,595, filed on Dec. 31, 2002.

(30) Foreign Application Priority Data

Jun. 20, 2002 (EP) .................................. 02013579

(51) Int. Cl.
A61B 5/05 (2006.01)
(52) U.S. Cl. ........................ 600/424; 600/407; 606/130; 434/262
(58) Field of Classification Search .................. 606/130; 600/424, 407; 434/262
See application file for complete search history.

(56) References Cited

U.S. PATENT DOCUMENTS

| 5,154,723 A | 10/1992 | Kubota et al. | |
|---|---|---|---|
| 5,460,490 A | 10/1995 | Carr et al. | |
| 5,513,637 A * | 5/1996 | Twiss et al. | 600/424 |
| 5,685,989 A * | 11/1997 | Krivitski et al. | 210/646 |
| 5,690,108 A * | 11/1997 | Chakeres | 600/424 |
| 5,697,899 A * | 12/1997 | Hillman et al. | 604/28 |
| 5,899,860 A * | 5/1999 | Pfeiffer et al. | 600/424 |
| 5,919,135 A * | 7/1999 | Lemelson | 600/407 |
| 6,282,437 B1 | 8/2001 | Franck et al. | |
| 6,331,181 B1 * | 12/2001 | Tierney et al. | 606/130 |
| 6,549,803 B1 * | 4/2003 | Raghavan et al. | 600/431 |
| 6,669,679 B1 * | 12/2003 | Savage et al. | 604/500 |
| 6,939,138 B2 * | 9/2005 | Chosack et al. | 434/262 |
| 7,266,227 B2 | 9/2007 | Pedain et al. | |
| 2002/0168618 A1 * | 11/2002 | Anderson et al. | 434/262 |
| 2004/0009459 A1 * | 1/2004 | Anderson et al. | 434/262 |

OTHER PUBLICATIONS

File history for U.S. Patent No. 7,266,227 dated Sep. 4, 2007.

* cited by examiner

Primary Examiner—Brian Casler
Assistant Examiner—John F Ramirez
(74) Attorney, Agent, or Firm—Renner, Otto, Boisselle & Sklar, LLP

(57) ABSTRACT

A method for positioning at least one catheter on a body in which a fluid is present includes performing a body-specific detection of anatomical structure and/or tissue structure. A position of the fluid in the body and/or the amount of fluid in the body are detected and at least one catheter is positioned such that at least a part of the fluid can be drained from the body. A method for simulating drainage of a fluid from an interstice of a body includes performing a body-specific detection of anatomical structure and/or tissue structure. A position of the fluid in the body and/or the amount of fluid in the body are detected and a location of at least one catheter on the body is set.

23 Claims, 3 Drawing Sheets

METHOD AND DEVICE FOR PREPARING A DRAINAGE

RELATED APPLICATION DATA

This application claims priority of U.S. Provisional Application No. 60/437,595, filed on Dec. 31, 2002, which is incorporated herein by reference in its entirety.

FIELD OF THE INVENTION

The present invention relates generally to a method and a device for preparing and assisting a drainage, such as an interstitial drainage, and, more particularly to positioning as optimally as possible at least one catheter in order to perform a drainage, as well as to a method and a device for introducing substances into a body.

BACKGROUND OF THE INVENTION

An excess amount of fluid in a person's head, such as in the interstitial space, due to an accident or a disease may lead to positive pressure and, therefore, to pressure on the brain. In order to avoid damage to the person's health, such positive pressure should be reduced as quickly as possible. To this end, a catheter can be positioned at a location in order to allow the fluid to drain off from the head. For such a drainage, a catheter can be attached at a position considered to be favorable and the interstitial fluid can be removed from the head through the catheter.

It has not been possible up to now to ensure that, as far as possible, all of the undesired fluid can be removed. Due to person-specific differences in body and tissue structures, catheters can easily be unintentionally positioned at less suitable locations, such that drainage can only be performed partially and another catheter may have to be positioned, making further operations necessary.

Introducing medicines into a body is known, for example, by infusion or injection, for example via a catheter. In the case of infusion, this can lead to a build up of positive pressure in the body, for example, due to a substance introduced into the interstice. The distribution of a substance introduced by infusion can depend on anatomical circumstances, the infusion pressure, the catheters used or on the nature of the introduced substance itself. Once the substance has been introduced, infusion can substantially no longer be influenced, except by changing the injection/infusion pressure.

SUMMARY OF THE INVENTION

It is an object of the present invention to propose methods and a device for preparing and assisting a drainage. In one embodiment, the invention includes optimally positioning at least one catheter, such as for interstitial drainage, which drainage may be performed as successfully as possible using as few catheters as possible. In general, the intention is preferably to drain a maximum amount of fluid with a minimum number of operations or catheter injections, such that minimally invasive operations can reduce side effects as far as possible, and possible treatment hazards for the patient can be largely excluded.

It is another object of the present invention to propose a method and a device for the improved introduction of substances into a body.

In accordance with a first aspect, the invention relates to a method for arranging at least one catheter on a body, such as on the head. The individual anatomical structure and the tissue structure can be determined body-specifically. Furthermore, the position of the interstitial fluid, i.e., the position relative to the surrounding tissue or body structures, the amount and the distribution are determined body-specifically.

In general, it can be advantageous to determine all the parameters, which influence how the fluid drains, such as, for example, the type or composition of the fluid, the pressure distribution, or other parameters. Imaging methods, such as nuclear magnetic resonance (MRI) methods, computer tomography (CT) methods, ultrasound methods, X-ray methods, SPECT methods, PET methods or other suitable methods can be used to determine the above-mentioned data and information.

Other examinations or measurements can also be performed, in order to determine a pressure, a pressure distribution of the interstitial fluid or a composition of the fluid. In one embodiment, the body-specific or head-specific information obtained in this way is evaluated and, on the basis of the evaluation, it is determined how to position optimally one or more catheters. To this end, one or more suitable positions for catheters can be predetermined, for example, in a body coordinate system or in a system-specific coordinate system. At these predetermined positions, one or more catheters can be positioned simultaneously or sequentially, to perform a drainage as optimally as possible. As much excess interstitial fluid as possible can be drained by a minimum number of injections. For example, a position for a catheter is determined at which a catheter can reduce a positive pressure prevailing in the body or head as quickly as possible. Further positions can optionally be determined in order to ensure that the interstitial fluid is drained as completely as possible.

In accordance with another aspect, the invention relates to a method for simulating fluid drainage through a catheter present in a body, such as in the interstice. Anatomical data on the structure of the body and/or the tissue are individually and body-specifically determined as described above, and the position, amount, distribution and/or type of interstitial fluid is determined body-specifically. It can be further assumed that one or more catheters are positioned simultaneously or sequentially at one or more predetermined locations. From this information, the course of drainage of fluid from the body can be simulated in order to find suitable positions for attaching one or more catheters or to verify their effectiveness.

Using a simulation in accordance with the invention, other drainage parameters may also be determined, optimized or verified, such as, for example a flow rate, a negative pressure present on the catheter, catheter geometry, and the like.

The simulation procedure can be performed on the assumption that the catheters are positioned on the body as described above.

The catheter(s) can be moved to the desired position on the body using known medical navigation methods. To this end, active or passive markers, such as, for example, reflective surfaces, can be attached to the catheter for use with the medical navigation system.

Parameters influencing the drainage of the interstitial fluid, such as, for example, the flow characteristics of a particular fluid, can be determined in a specific type of tissue and used to determine the optimal position of a catheter or for a simulation. Such body-specific parameters can, for example, be stored in a database and can be determined by examination, before the method in accordance with the invention is performed.

Parameters describing the properties of the fluid to be drained may likewise be provided in a database and can be used, for example, to plan the arrangement of a catheter or to simulate draining the fluid. The viscosity, i.e., the interaction between a particular fluid and a particular tissue, the flow characteristics in a particular type of tissue, or other information can be stored in a database for use in conjunction with the methods of the present invention.

In one embodiment, a method in accordance with the invention can be performed using a database containing information and parameters for one or more different types of catheter available. For example, the database may include data on the geometry, such as the diameter, of the catheter, the material, the surface and its properties when interacting with tissue or fluids to be drained. One or more catheters can be selected automatically and/or by an operator based on the above data or other factors.

Information on possible, advantageous ways of adapting, changing or processing the catheters to be used can be determined and outputted in order to arrange at least one catheter on a body. For example, an optimal catheter length can be determined, such that a standardized catheter can be cut to a desired length or modified in some other way.

In addition, other parameters influencing drainage, such as a negative pressure to be applied to a catheter or a suction force, can be determined. In this way, the drainage rate of the interstitial fluid, typically in the range of a few milliliters per hour, can be influenced and regulated.

In one embodiment, a verification method can be performed. Additional data can be captured intra-operatively, for example, using an imaging method or other measurement, in order to determine the body-specific structures changed by the drainage and/or the position, distribution and amount of the interstitial fluid after partial or complete drainage. This information can be used to verify that a drainage was carried out. In addition, this information can be used to correct or reposition one or more catheters, as may be necessary, or to replace catheters, to change the flow rate or to influence other parameters relevant to drainage. In addition, the verification can take into account, for the further course of the drainage, that an already reduced pressure or drained fluid may cause a change in the position of a body or tissue structure and that the drainage plan may have to be changed, for example, by repositioning a catheter or changing parameters.

In accordance with another aspect, the invention relates to a method for controlling infusion. A substance can be introduced into a body, for example, using one or more catheters, at or near at least one location on the body. A positive or negative pressure can be applied to the body at or near at least one other location, such as at a region of the body or interior of the body, such that the distribution of a substance introduced into the body at the at least one location can be influenced by applying the positive or negative pressure to other locations on the body. It is thus possible to establish preferred flow or spreading directions for a substance introduced, in order to introduce the substance as precisely as possible into particular regions of the body. Furthermore, applying a negative pressure can reduce or remove a possibly damaging internal pressure in the body, which would be further increased by introducing a substance. To apply a negative pressure, catheters can, for example, be positioned in the interstice or in the ventricles, in order to apply a negative pressure to at least one desired location on the body and to influence, for example, the distribution or flow direction of a substance introduced into the body.

In general, the method for controlling infusion can be used in combination with one or more of the method steps described above. For example, based on body-specific anatomical and/or tissue structure data, the catheters can be suitably positioned to introduce a substance and/or to apply a positive pressure or a negative pressure. An infusion process can be simulated to determine the distribution of a substance in the body. Furthermore, the catheters can be positioned using medical navigation methods. It is also possible to use information stored in databases to plan or perform the method as described above.

In accordance with another aspect, the invention relates to a computer program, which can be loaded into the memory of a computer and includes sections of software code. One or more steps of the methods described above can be performed when the program is run on a computer. The invention further relates to a computer program product stored on a computer-compatible medium or data carrier and including the computer program just described.

In accordance with another aspect of the invention, a device for simulating fluid drainage from a body includes a data capture device for capturing structural data of the body and/or the position of a fluid in a body. For example, the data capture device can include a nuclear spin tomograph and a computer system for determining the arrangement of at least one catheter on a body. In addition, the simulation device can include an input device for inputting the position of at least one catheter in order to simulate the fluid drainage from the body, using the body-specific and fluid-related data determined by the data capture device.

In general, the present invention relates to a device using which one or more of the method steps described above can be performed. To this end, for example, databases can be provided for storing parameters or characteristics of one or more catheters, particular body parameters, fluid parameters and/or drainage parameters.

In order to perform the drainage, a device for setting the drainage flow rate, such as, for example, a pump, can be provided. The pump can generate a desired suction action or a negative pressure in order to perform drainage as planned and/or simulated by the methods in accordance with the invention.

Known methods using markers, such as the VectorVision® system, distributed by the applicant, can be used to navigate one or more catheters, in order to ensure that said catheters are optimally positioned and seated.

With respect to a device and methods for administering a substance, which may be used in combination with the invention, reference is made to European patent application No. 01 128 614.3, filed by the Applicant on Nov. 30, 2001, which is incorporated by reference in its entirety, and commonly owned corresponding U.S. patent application Ser. No. 10/075,108, which is incorporated herein by reference in its entirety.

BRIEF DESCRIPTION OF THE DRAWINGS

The invention will now be described by way of preferred embodiments.

DETAILED DESCRIPTION OF THE INVENTION

Figure 1:
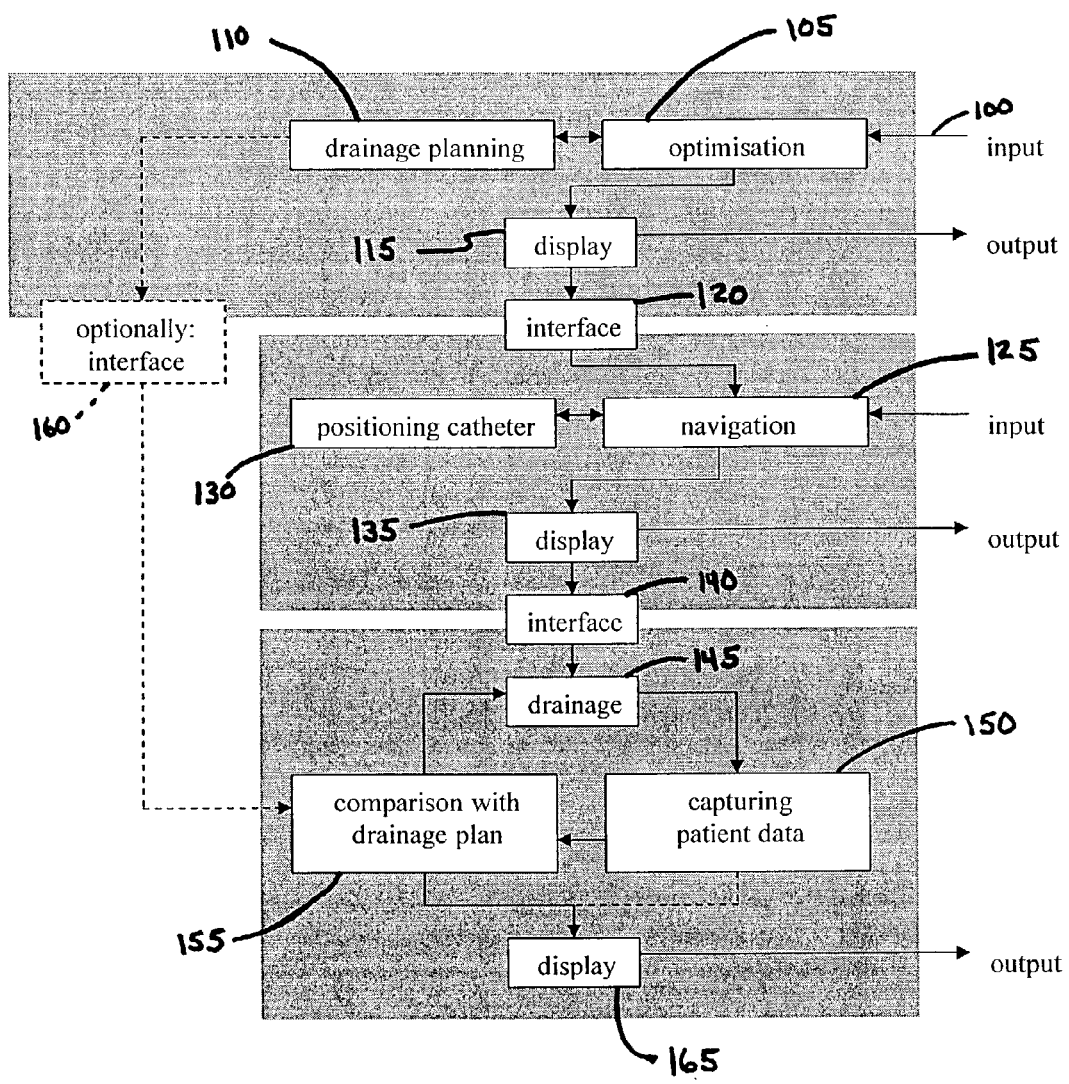
FIG. 1 is a schematic flow diagram of a method for planning and performing a drainage in accordance with the invention.

FIG. 1 shows a schematic flow chart for preparing and performing drainage. As shown in FIG. 1, patient data can be inputted 100, for example, from a nuclear spin tomograph, which can be used to determine one or more particular regions for positioning catheters for drainage and to plan the drainage to be performed. The patient data can be obtained, for example, using the nuclear spin resonance system 3 (shown schematically in FIG. 3) once a patient to be treated has been examined. Using parameters for the properties of the tissue structures and for various types of catheters, stored, for example, in databases, one or more catheters suitable for the drainage can be selected, once the exact position of the interstitial fluid to be drained and of the body or tissue structure has been determined.

The obtained parameters of the body or patient can be used together with the catheter parameters and the fluid parameters, also, for example, stored in databases, to plan or simulate the drainage. In this way, the course of the drainage to be performed can be optimized 105 by balancing the conditions of removing as great a proportion of the interstitial fluid as possible from the body structure or the target tissue, while doing so in as few operations as possible. In general, as few catheters or needles should be positioned as possible and the catheters or needles should be supplied through as few access points as possible. This optimized planning 105, 110 of the drainage can be outputted via a display 115, such that, for example, a two-dimensional or three-dimensional representation can be outputted by imaging various incision planes, in order to display the resultant drainage plan.

The drainage plan produced in this way is transmitted via an interface 120 to a medical navigation system 125, such as, for example, the VectorVisionŌ system (shown schematically in FIG. 3) in order to position 130 the selected catheter or catheters at the predetermined locations on the body, based on the planning data. Medical navigation systems are known and described in, for example, co-owned U.S. Pat. No. 6,351,659, which is incorporated herein by reference in its entirety. The catheters can be positioned automatically, for example, using a robot. Alternatively, the catheters can be positioned by hand, if guided by a navigation system, wherein a display device 135, 140 can indicate whether a catheter has been positioned correctly or whether it still has to be moved in a particular direction.

Once the catheter or catheters have been successfully positioned 130, the actual drainage 145 is performed using the drainage parameters predetermined by the plan 110, such as, for example, a flow rate, which can be constant or changing with time. To this end, patient data can be again captured 150 to determine the actual distribution of the fluid in the body or tissue. Using the parameters predetermined by the plan and the drainage simulation results based on them, a comparison 155, 160 can be made between the actual drainage, (e.g., the distribution of the partially drained fluid), and the predetermined distribution of fluid (also referred to as a verification). As appropriate, the parameters, such as, for example, the flow rate, the drainage amount or a pressure or suction applied to the catheter for performing drainage, can be altered, preferably taking into account known active mechanisms, in order to obtain the desired, planned drainage result. Again, the actual distribution of the interstitial fluid measured can preferably be outputted together with any deviations and correction methods via a display 165, for example, to enable an operator to intercede in the drainage method manually.

Figure 2:
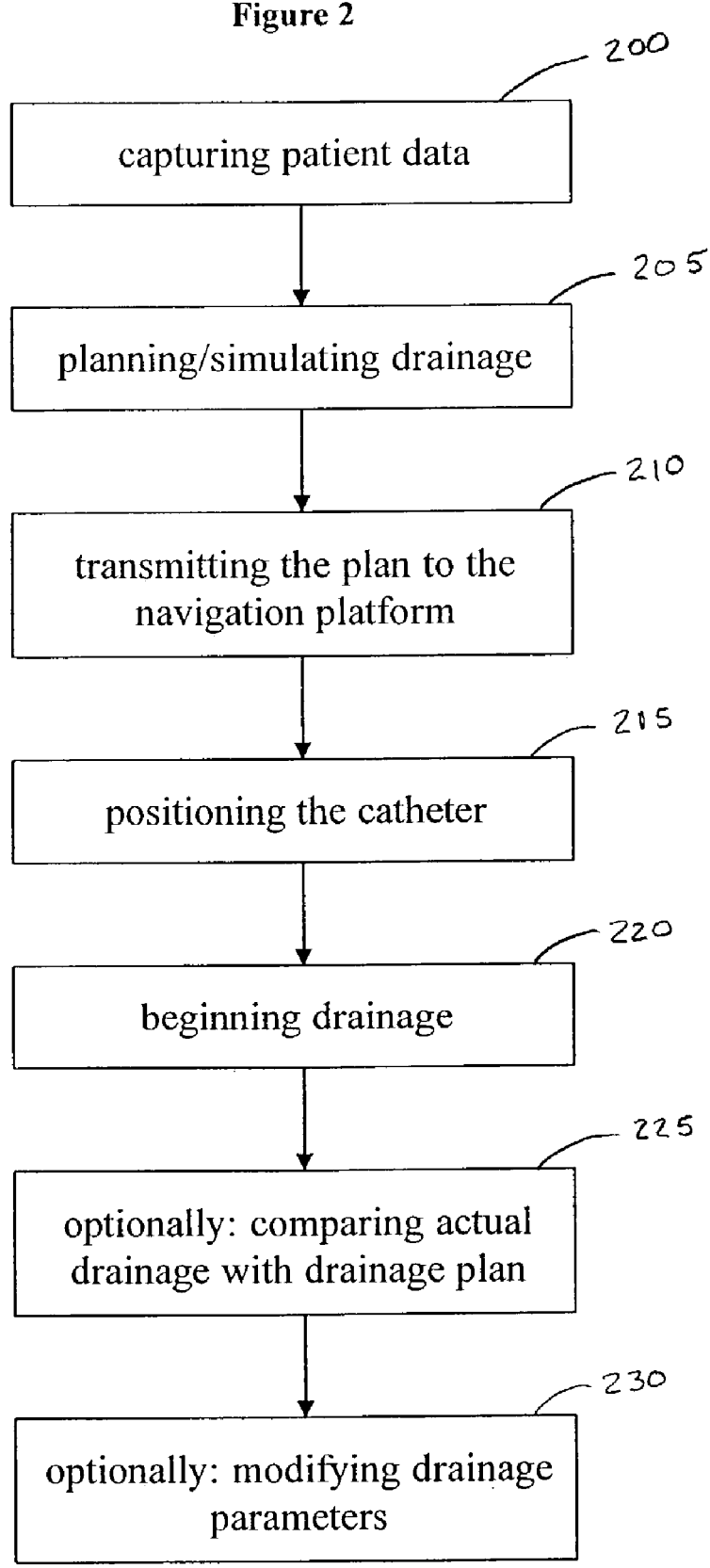
FIG. 2 is a flow chart illustrating a method of performing a drainage in accordance with the invention.

FIG. 2 schematically shows a simplified sequence of planning and performing drainage. Firstly, patient data can be captured 200 using a diagnostic imaging method, such as, for example, a nuclear spin resonance method. This step can be effective to obtain the current patient parameters, such as, for example, tissue density, pressure and position of a fluid to be drained. Using the patient parameters determined in this way, as well as catheter and drainage parameters obtained from a database and/or predetermined for a specific drainage, the drainage can be planned and/or simulated 205. Based on the parameter data determined in this way, the drainage plan is transmitted to a navigation platform 210, by which the catheter or catheters are to be positioned 215 on the patient, as provided for in the drainage plan. Drainage begins 220 once the catheters have been positioned and is performed using the planned and as appropriate simulated parameters. As shown in FIGS. 1 and 2 a comparison 155, 225 is optionally made between the drainage actually performed and the drainage plan. In the event of deviations, the corresponding parameters are optionally modified 230 and can be fed back into the planning and/or simulation program 205. The entire loop can then be run again.

Figure 3:
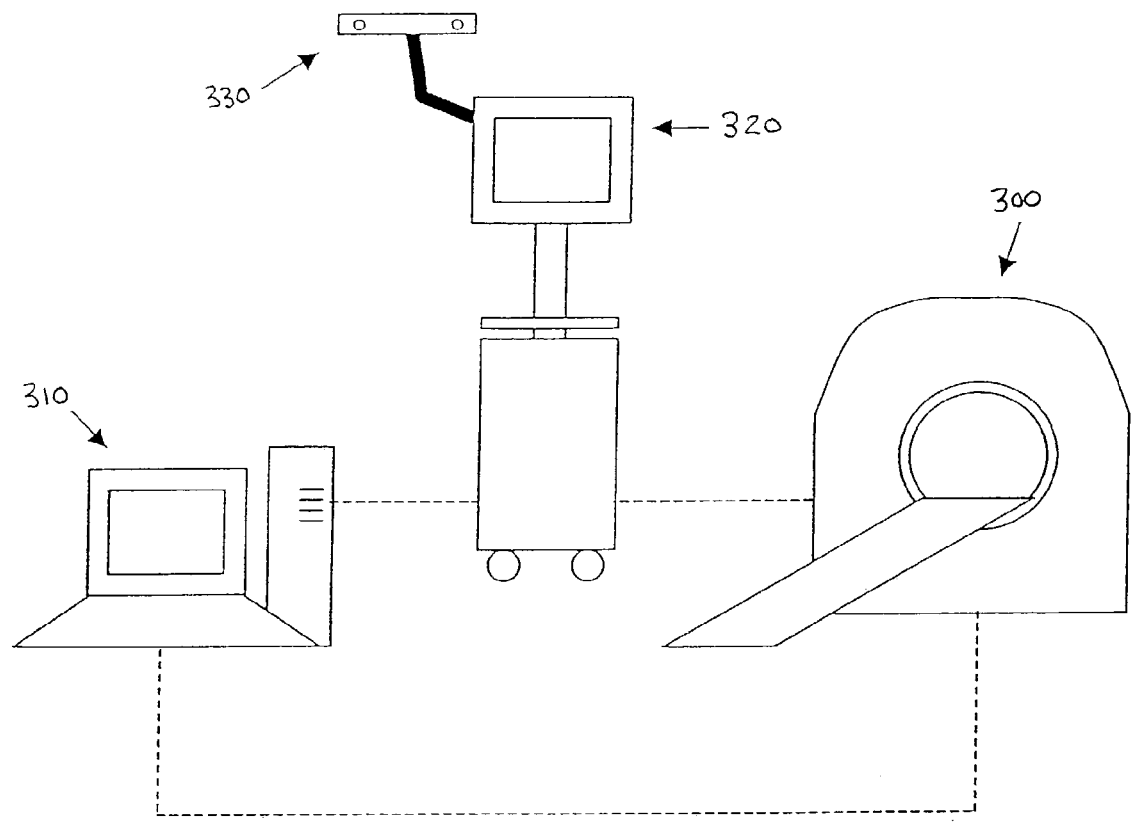
FIG. 3 is a diagrammatic illustration of a device, which can be used to plan and perform a drainage in accordance with the invention.

FIG. 3 schematically shows a device which may be used to plan, simulate and/or perform a drainage. In one embodiment, patient data (e.g., in the form of a nuclear spin tomograph) can be obtained using a nuclear spin resonance system 300 and transmitted to a planning system 310 and to a navigation system 320. Using the navigation system 320, the catheter or catheters can be positioned at a desired location on the body using, for example, known reflectors or markers attached to one or more of the catheters. In this embodiment, positional data of the markers can be captured by infrared cameras 330, as is known in the art. The planning system 310 determines the suitable catheter parameters and drainage parameters for a predetermined drainage to be performed, using the patient parameters detected or otherwise determined by the nuclear spin resonance system 300, in order to perform the drainage.

What is claimed is:

1. A method for positioning at least one drainage catheter on a patient body in which a fluid is present, said method comprising:

(a) performing a body-specific detection of at least one of (i) anatomical structure or (ii) tissue structure on the patient body;

(b) detecting at least one of (i) a position of the fluid in the patient body relative to the surrounding tissue or anatomical structures or (ii) the amount of the fluid in the patient body using at least one of (i) a nuclear spin resonance method (MRI), (ii) computer tomography method (CT), (iii) an X-ray method, (iv) a SPECT method or (v) an ultrasound method; and (c) based on steps (a) and (b), positioning at least one catheter such that at least a part of the fluid can be drained from the patient body.

2. The method as set forth claim 1, wherein step (a) is performed using at least one of (i) a nuclear spin resonance method (MRI), (ii) computer tomography method (CT), (iii) an X-ray method, (iv) a SPECT method or (v) an ultrasound method.

3. The method as set forth in claim 1, wherein at least one catheter is positioned on the body using a navigation method.

4. The method as set forth in claim 1, further comprising:
storing flow characteristics of the fluid in a database; and
using the stored flow characteristics to simulate the fluid drainage.

5. The method as set forth in claim 1, further comprising:
storing parameters of the fluid to be drained from the body in a database; and
using the stored parameters to simulate the fluid drainage.

6. The method as set forth in claim 1, further comprising:
storing parameters of the at least one catheter in a database; and
using the stored parameters to simulate the fluid drainage.

7. The method as set forth in claim 1, further comprising: outputting individually adapted data for adapting or modifying at least one predetermined standard catheter.

8. The method as set forth in claim 1, further comprising: determining at least one of (i) flow rate of the fluid to be drained or (ii) a negative pressure to be applied to the catheter.

9. The method as set forth in claim 1, further comprising: capturing additional data after the drainage has been performed to verify or modify the drainage.

10. A method for planning a drainage of a fluid from an interstice of a patient body, the method comprising:
   (a) acquiring patient body-specific data representative of at least one of (i) anatomical structure or (ii) tissue structure on the patient body;
   (b) acquiring data representative of at least one of (i) a position of the fluid in the patient body relative to the surrounding tissue or anatomical structures or (ii) an amount of the fluid in the patient body using at least one of (i) a nuclear spin resonance method (MRI), (ii) computer tomography method (CT), (iii) an X-ray method, (iv) a SPECT method or (v) an ultrasound method;
   (c) selecting a location of at least one catheter on or in the patient body;
   (d) performing a computer-based simulation of the drainage based on:
      the acquired data representative of at least one of (i) anatomical structure or (ii) tissue structure;
      the acquired data representative of at least one of (i) position of fluid in the patient body or (ii) amount of fluid in the patient body; and
      the selected location of at least one catheter on or in the patient body.

11. The method as set forth in claim 10, further comprising: storing flow characteristics of the fluid in a database; and using the stored flow characteristics to simulate the fluid drainage.

12. The method as set forth in claim 10, further comprising: storing parameters of the fluid to be drained from the body in a database; and using the stored parameters to simulate the fluid drainage.

13. The method as set forth in claim 10, further comprising: storing parameters of the at least one catheter in a database; and using the stored parameters to simulate the fluid drainage.

14. The method as set forth in claim 10, further comprising: outputting individually adapted data for adapting or modifying at least one predetermined standard catheter.

15. The method as set forth in claim 10, further comprising: determining at least one of (i) flow rate of the fluid to be drained and (ii) a negative pressure to be applied to the catheter.

16. The method as set forth in claim 10, further comprising: capturing additional data after the drainage has been performed to verify or modify the drainage.

17. A computer program stored on a non-transitory computer-readable medium for planning a drainage of a fluid from an interstice of a patient body, wherein the program instructs a computer to:
   (a) acquire patient body-specific data representative of at least one of (i) anatomical structure or (ii) tissue structure on the patient body;
   (b) acquire data representative of at least one of (i) a position of the fluid in the patient body relative to the surrounding tissue or anatomical structures or (ii) an amount of the fluid in the patient body using at least one of (i) a nuclear spin resonance method (MRI), (ii) computer tomography method (CT), (iii) an X-ray method, (iv) a SPECT method or (v) an ultrasound method;
   (c) select a location of at least one catheter on or in the patient body; and
   (d) perform a computer-based simulation of the drainage based on:
      the acquired data representative of at least one of (i) anatomical structure or (ii) tissue structure;
      the acquired data representative of at least one of (i) position of fluid in the patient body or (ii) amount of fluid in the patient body; and
      the selected location of at least one catheter on or in the patient body.

18. A device for simulating a drainage of a fluid from a patient, comprising:
   a data capture device that captures data indicative of at least one of (i) structure of the patient or (ii) position of a fluid in the patient relative to surrounding tissue or anatomical structures;
   an input device for inputting a position of at least one catheter, and
   a computer system that simulates fluid drainage on the basis of the captured patient data and the position of the catheter.

19. The device as set forth in claim 18, further comprising a device for determining the position on the patient of the at least one catheter.

20. A method of planning a drainage of a fluid from an interstice of a patient, the method comprising:
   providing an initial drainage plan based on known or recorded patient data, catheter parameters and fluid parameters; and
   performing a computer-based simulation of the drainage according to the initial drainage plan, the computer-based simulation generating simulated drainage results.

21. The method as set forth in claim 20, further comprising: based on the simulated drainage results, modifying the initial drainage plan.

22. The method as set forth in claim 21, further comprising: performing an actual drainage according to the modified initial drainage plan;
   recording results of the actual drainage;
   comparing the actual drainage results with the simulated drainage results.

23. The method as set forth in claim 22, further comprising: based on the comparison between the actual drainage results and/or the simulated drainage results, further modifying the modified initial drainage plan; and
   performing a computer-based simulation of the drainage according to the at least twice-modified initial drainage plan.

* * * * *